(12) United States Patent
Ronacher

(10) Patent No.: US 8,986,934 B2
(45) Date of Patent: Mar. 24, 2015

(54) DEVICE FOR THERMALLY REGULATING A ROTATIONALLY SYMMETRICAL CONTAINER

(75) Inventor: Bernhard Ronacher, Linz (AT)

(73) Assignee: Anagnostics Bioanalysis GmbH, St. Valentin (AT)

( * ) Notice: Subject to any disclaimer, the term of this patent is extended or adjusted under 35 U.S.C. 154(b) by 91 days.

(21) Appl. No.: 13/061,054

(22) PCT Filed: Aug. 14, 2009

(86) PCT No.: PCT/AT2009/000312
§ 371 (c)(1),
(2), (4) Date: Feb. 25, 2011

(87) PCT Pub. No.: WO2010/022417
PCT Pub. Date: Mar. 4, 2010

(65) Prior Publication Data
US 2011/0195417 A1    Aug. 11, 2011

(30) Foreign Application Priority Data
Aug. 29, 2008    (AT) ................. A 1350/2008

(51) Int. Cl.
| | | |
|---|---|---|
| C12Q 1/68 | (2006.01) | |
| C12P 19/34 | (2006.01) | |
| B01L 7/00 | (2006.01) | |
| B01L 3/00 | (2006.01) | |
| G01N 33/543 | (2006.01) | |

(52) U.S. Cl.
CPC . B01L 7/52 (2013.01); B01L 3/502 (2013.01); B01L 3/5021 (2013.01); G01N 33/54366 (2013.01); *B01L 2300/0636* (2013.01); *B01L 2300/0832* (2013.01); *B01L 2400/0406* (2013.01); *B01L 2400/0409* (2013.01)
USPC .............. 435/6.12; 435/6.1; 435/6.11

(58) Field of Classification Search
CPC ......... B01L 3/502; B01L 3/5021; B01L 7/52; G01N 33/54366; C12Q 1/6883; C12Q 1/6827
See application file for complete search history.

(56) References Cited

U.S. PATENT DOCUMENTS

| | | | |
|---|---|---|---|
| 4,531,932 A | 7/1985 | Luppi et al. | |
| 5,433,080 A | 7/1995 | Boeckel | |
| 7,927,546 B2 * | 4/2011 | Ronacher et al. | ............... 422/72 |
| 2005/0026277 A1 * | 2/2005 | Festoc | ........................ 435/287.2 |

FOREIGN PATENT DOCUMENTS

| | | |
|---|---|---|
| DE | 199 39 252 | 4/2001 |
| EP | 1 845 372 | 10/2007 |
| JP | 2000005639 | 1/2000 |
| JP | 2001153487 | 6/2001 |
| WO | WO 00/23190 | 4/2000 |
| WO | WO 01/89692 | 11/2001 |
| WO | WO 03/000428 | 1/2003 |
| WO | WO 03/100401 | 12/2003 |
| WO | WO 2007/041734 | 4/2007 |

OTHER PUBLICATIONS

International Search Report issued in PCT/AT2009/00312, dated Nov. 24, 2009.

* cited by examiner

*Primary Examiner* — Young J Kim
(74) *Attorney, Agent, or Firm* — Norton Rose Fulbright US LLP

(57) ABSTRACT

The present invention relates to a device for thermally regulating a rotationally symmetrical container having a lateral surface and/or a base surface, said device comprising at least one thermal-regulation block which is suitable for accommodating the container and has at least two thermal-regulation elements, wherein the thermal-regulation elements in the at least one thermal-regulation block exchange heat with the lateral surface and/or with the base surface of the container to be thermally regulated.

25 Claims, 6 Drawing Sheets

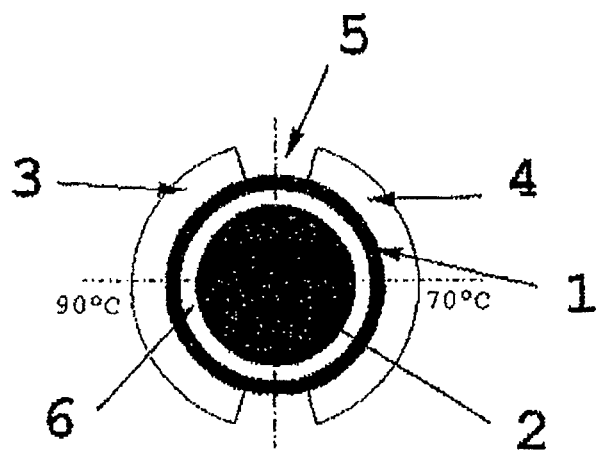
Fig. 1
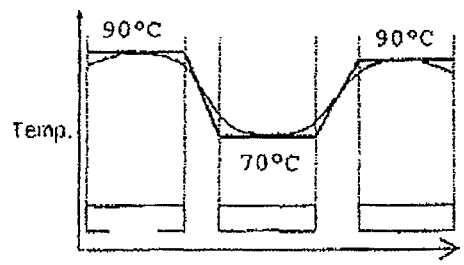
Fig. 2
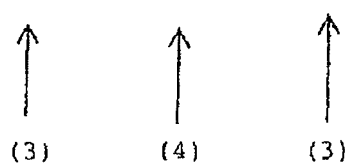

DEVICE FOR THERMALLY REGULATING A ROTATIONALLY SYMMETRICAL CONTAINER

This application is a national phase application under 35 U.S.C. §371 of International Application No. PCT/AT2009/000312 filed 14 Aug. 2009, which claims priority to Austrian Application No. A 1350/2008 filed 29 Aug. 2008. The entire text of each of the above-referenced disclosures is specifically incorporated herein by reference without disclaimer.

The present invention relates to a device for tempering (thermally regulating) a rotationally symmetrical container.

Stepwise tempering, in particular the alternate heating and cooling of liquids to control biochemical tests, is of great importance in the combination of primers and in the use of heat stable DNA polymerases in the polymerase chain reaction (PCR), and in the formation of nucleic acid double strands in the context of hybridization events (Southern hybridization). The development of PCR was followed by the arrival of other enzymes such as ligases and kinases, etc. They all operate on the principle that the liquid and the components contained therein (reactants) are tempered and that the liquid constitutes a reaction unit (uniform temperature and composition).

Such reactions, however, do not just occur in pure liquids, but may also occur with solid phases, whereupon such phases can be used to carry out solid phase reactions. To this end, at least one reactant is immobilized on a solid phase. In its simplest form, slides (usually of glass) can be used as solid phases/supports; they are placed on a metal block and covered with a liquid phase. Evaporation can be minimized by using a hood (chamber). This means that a sealed volume is produced at least during the reaction period. The reactants, such as primers for a PCR reaction, can be covalently immobilized on the surface of the slide and constitute the starting point for the test. In general in such systems, the mobile phase can again be considered to be a unit and they are essentially identical in composition.

Thermostatted microfluidics systems constitute a third system. In this case, the mobile phase (with all of the reactants) is pumped through a predefined path (channel, capillary). Thus, the mobile phase traverses zones in which the walls (boundaries) are at different temperatures (which may be constant). The advantage of this system is that the temperature in the mobile phase can change rapidly (see, for example, WO 00/23190, WO 01/89692).

U.S. Pat. No. 5,433,080, JP 2000005639, JP 2001153487 and EP 1 845 372 describe centrifuges which can be heated.

U.S. Pat. No. 4,531,932 describes a plasmapheresis device which comprises a container in which a rotationally symmetrical rotor is arranged. In order to prevent blood in that device from cooling, the centre of the rotor comprises tempering elements.

The prior art discloses many methods and devices for tempering liquids during analysis, in particular for PCR methods, in which two areas are of great significance:
a) rate and accuracy of heating and cooling rates;
b) number of different reactions.

Currently, the fastest heating and cooling rates which are still exact which can be obtained with tempering blocks formed from metal in the nucleic acid amplification reaction (PCR) are in the region of 5-7° C. per second. In this regard, the accuracy of the temperature to be obtained is of particular importance, since the annealing temperature or melting temperature of DNA must not be overshot or indeed undershot by much since this could lead to unwanted side reactions. This means that the target temperature is approached very slowly. This means that both heating and cooling periods are substantially longer, meaning that as regards accuracy, now both the quantity and the composition of the mobile phase must be taken into account. In micro-fluidics systems, wherein all reactants are in solution and are transported in capillaries, for example, that problem is solved by applying constant temperatures to the temperature zones through which the capillaries are guided. However, that system suffers from the disadvantage that all of the reactants have to be transported together in the mobile phase. Combination with a solid phase reaction system is thus not possible.

Particularly with soluble primers (PCR), it is known that with the simultaneous (parallel) use of many different primers, unwanted reactions may occur. This then results in signals which may lead to false-positive or false-negative results. Thus, multiplex systems (several test reactions in a single test), especially in the field of testing for nucleic acids, is in practice only of limited application. This can be avoided by dividing the samples into several aliquots which can then be analyzed in individual tests. Dividing small samples gives rise to large, unavoidable statistical errors on the one hand and on the other hand, takes much longer and costs much more.

Thus, an aim of the present invention is to provide a device which can produce different temperature zones in a single container, for example in order to carry out a plurality of different test reactions simultaneously in a single or in several small test systems. A further aim is to provide a device that can allow fast and precise heating and cooling cycles to be carried out. A further aim is to guide reactants (primers) immobilized in said individual container alternately through the various temperature zones.

The present invention concerns a device for tempering a rotationally symmetrical container, having a lateral surface and/or a base surface comprising at least one tempering block for accommodating the container having at least two tempering elements, wherein the tempering elements of the at least one tempering block can be brought into heat exchanging contact with the lateral surface and/or with the base surface of the container to be tempered.

By providing a tempering block with more than one tempering element (at least two, preferably at least three, four, five, six, seven, eight, nine or ten), it is possible by virtue of the device of the invention to produce zones with different temperatures in one container which can be brought into heat exchanging contact with the tempering block. By providing zones with different temperatures, different temperature conditions can be produced within the container. This is advantageous, for example, when different enzymes which exhibit reaction optima at different temperatures are immobilized on the inner lateral surface. In this manner, reactions with different reaction conditions can be carried out simultaneously in the container.

The container which can be accommodated in the tempering block can be rotationally (radially) or non-rotationally (radially) mounted in the tempering block. If the inserted container is rotationally mounted, it is not capable of rotating within the tempering block.

The thermal regulating block has a shape which is suitable for accommodating a rotationally symmetrical container, insofar as the tempering elements in the tempering block can be brought into heat exchanging contact with at least the base surface or the lateral surface of the container. In this regard, the shape of the tempering block is preferably equivalent to that of the container. Heat exchanging contact between the tempering elements and the container can thus be obtained so that both elements are in direct contact or that means are provided between the lateral surface/base surface of the container and the tempering element (for example heat conducting means).

In order to insert the container to be tempered in the tempering block, the container is preferably arranged so as to be displaceable with respect to the at least one tempering block. This means that after use, the container can also be removed from the tempering block. If necessary, the tempering block may have a locking device which prevents translational and/or radial movement of the container relative to the tempering block. This prevents the container from being moved in an uncontrolled manner relative to the tempering block during use of the device, which could otherwise result in unwanted temperature differences. Thus, in operation, the container which is in heat exchanging contact with the tempering elements is preferably fixed relative to the tempering block. This means that as soon as the container is brought into heat exchanging contact, it can be fixed in translation.

Various methods or method steps can be carried out using the device of the invention. Thus, the device is suitable for heating and cooling liquids for the purposes of carrying out specific biochemical reactions (for example denaturing DNA, PCR, ligase reactions, general enzyme reactions, etc.).

The container may have any shape as long as it is rotationally symmetrical (for example cylindrical, conical, truncated conical). This means that if necessary, the container can be rotated in the tempering block without interrupting the heat exchanging contact between the container and the tempering block. Furthermore, this shape also means that a rotor which can be rotated in the container can be inserted into a container which is fixed in rotation, and the lateral surface of this rotor forms an annular gap with the inner lateral surface of the container such that the separation of the lateral surface of the rotor and the inner lateral surface of the container remains essentially constant during rotation. Preferably, the rotationally symmetrical container is in the shape of a cylinder, since this shape means that the path followed by every point on the lateral surface of the container is the same when rotated. This guarantees that the container will be equally tempered over the entire length.

The shape of the tempering elements also corresponds to the shape of the container. Thus, for example, they may have the shape of jaws. They may also be shaped as rods, rectangles, or circular (elliptical) surfaces, as well as wires or fibres.

The type of heat transport may be by means of contacting surfaces (preferably metal surfaces), or by means of contactless heat exchange, for example by radiation energy (infrared, microwaves), tempering gases or liquids, friction, electrical charge exchange, etc.).

The container is suitable for the analysis of gaseous and/or liquid samples and has a rotationally symmetrical rotor that can be inserted in the container, whereby an annular gap is provided between the container and the rotor and the rotor has at least one flow channel to convey liquids and/or gases into and/or out of the interior of the container.

Devices for analysing liquid samples which have a rotor inside them are already known in the art (see, for example, WO 2007/041734 and WO 03/100401). These containers are particularly suitable for use in a device of the invention.

In accordance with a preferred embodiment of the present invention, biomolecules are immobilized on the surface of the rotor. Providing biomolecules on the surface of the rotor means that they can be moved through the medium inside the container during the course of rotation. Thus, the biomolecules immobilized on the surface are exposed to different temperatures during the course of rotation depending on which tempered zone is being traversed.

Alternatively, biomolecules are advantageously immobilized on the surface of the base surface opposite to the tempering elements.

In a further embodiment of the present invention, the biomolecules may be immobilized on the base surface of the container.

The device of the invention is particularly suitable for use in methods in which different temperatures are required. This is the case, for example, in the amplification of nucleic acids. Thus, the biomolecules immobilized on the rotor or on the inner lateral surface are preferably nucleic acids, such as primers, probes or the like, or heat-stable enzymes.

The tempering elements within the tempering block may be arranged in different manners. An arrangement consisting of only one tempering element for heating and cooling the entire container (mobile and stationary phase) is not advantageous. This indeed enables the device of the invention to be used with arrays as a multiplex system, but has the disadvantage that the heating and cooling rates are relatively slow because of the relatively large volume inside the container. Thus, the precision is only low since the heating and cooling elements will always overshoot to some extent. In order to increase the heating and cooling performance, the heating elements are divided into two zones. This means that two or more elements or two or more Peltier elements can be used, the advantage being that both heating elements can be used at different temperatures.

Surprisingly, this means that two different temperature zones can be generated consistently inside the incubation volume. Even when a cylinder inside the container is turned slowly, the temperature zones can be maintained. This means that, for example, the primers on the rotor or the container surface (which extend into the mobile phase) also experience these temperature differences. This means that for two constant temperature zones, a thermoprofile (thermocycle) can be produced for the primer and thus for the individual tests on the mobile phase. In particular, this arrangement enables several thousand primers (tests per spot) to be used in one test, provided with a consistent heating and cooling system for two defined temperature zones, whereupon a fast and precise test is carried out. In this manner, the test setup is intact throughout the analysis (sealed reaction volume), the reactions are consistent and are not interrupted (opening of container) and, moreover, can also be measured in real-time.

The tempering elements in the tempering block are independently and preferably provided as cooling elements or heating elements. The tempering elements can be used both for heating and for cooling. Control may, for example, be accomplished via a computer or a control unit. When the device of the invention is in use, the tempering elements may be used exclusively as cooling elements or exclusively as heating elements. Alternatively, the tempering elements may carry out alternating functions (heating or cooling elements).

In accordance with a preferred embodiment of the present invention, the tempering elements are Peltier elements. Electrical resistances (electrical resistance heating), elements filled with liquids or gases (liquid elements (tubes etc) or gas flow heating), as well as radiative heating (infrared radiation, microwaves (infrared emitter, microwave transmitter or light emitters), etc, are also suitable.

In order not to affect or to barely affect the accuracy of the temperature control at the tempering elements, a space or an insulating material is preferably provided between the tempering elements of the at least one tempering block. In the simplest embodiment, this is air. Foamed plastics, glass or ceramic materials may also be used.

In a further aspect, the present invention concerns the use of a device in accordance with the invention for the amplification of nucleic acids (for example PCR). In this case, primers are preferably bound directly or via a chemical linker to the inner lateral surface or base surface of a container. In such an embodiment, either the container can be moved radially in the tempering device or, if it is fixed radially, the tempering elements can be alternately cooled or heated (following the PCR cycling) to the required temperatures. In accordance with a particularly preferred embodiment of the present invention, the primers are bound to the surface (lateral surface) of a rotor which can be inserted into the container. In this embodiment, the container is fixed in rotation. Preferably, primers of different types can thus be immobilized on the rotor surface, in order to carry out a plurality of amplifications of various nucleic acids.

With the present invention, it is in particular possible to carry out nucleic acid amplifications. In this regard, the device of the invention can be arranged so that it is capable of accommodating a container that is itself capable of accommodating a rotationally symmetrical cylinder (rotor) on the lateral surface of which spots (nucleic acids, primers) are immobilized. Between the inserted cylinder and the inner wall of the container is an annular gap which can accommodate liquids (such as PCR solutions, etc, for example). During rotation of the cylinder in the container, the nucleic acid molecules bound to the cylinder run through a temperature profile in the surrounding liquid which is provided by the tempering elements of the device of the invention. The number of thermozones and the temperatures therein are fully adjustable since each tempering element can be individually controlled. In this scenario, the stationary phase (immobilized spots) becomes the mobile phase as regards the temperature. This is also the essential distinction over microfluidics, where liquids are sent through channels and thus pass through zones at different temperatures. The disadvantages here are that all of the reaction components in the mobile phase have to be jointly transported. A reaction at the stationary phase is thus impossible and so using several simultaneous tests is not possible.

Preferably, the container and/or the rotor of the device of the invention are divided into separate chambers or regions.

Many simultaneous tests can be carried out by immobilizing several identical or different reactants in predetermined reaction regions on a solid phase (primer extension, EP 0 972 081). If the immobilized reactants are covered with a mobile phase (liquid) which contains all the general reactants and the sample components, then the liquid and the immobilized primers which extend into it can be tempered. In the embodiment of the invention, tempering occurs by transfer of the solid phase (immobilized primer) through different temperature zones. The temperature zones are defined by a solid boundary (container or generally a lid) of the volume for the mobile phase. In a special embodiment, the temperature zones are defined within the container by the contact surface of the tempering elements placed thereon.

When the rotor in the container or the container itself rotates, the immobilized primers pass through the different temperature zones which are set up by the tempering elements. To this end, the tempering elements are preferably at temperatures which are normal for such methods. The heating and cooling times are thus substantially shortened (from 60 sec to 5 sec) and overshooting is completely prevented since the heating elements themselves are at constant temperatures.

Furthermore, the device of the invention can be used to carry out enzyme reactions such as DNA polymerase reactions (solid phase amplification, arrayed primer extension (APEX)), DNA ligase reactions, DNA methyl transferase reactions, restriction endo- and exo-nuclease reactions, oxidoreductase, hydrolase, ligase, lyase, isomerase, phosphatase, kinase, methylase and transferase reactions.

Many different tests, such as those based on binding of primers to DNA/RNA, for example, can be carried out using the device of the invention in a particularly convenient manner. Some of the various primers which are immobilized on a surface might possibly then start to react with portions of a biological sample (blood extract). This reaction should then run in a manner similar to an isolated test and thus will not be influenced by other primers which are also present. Thus, the test system would be parallel in type. Dividing up the sample for individual tests is thus superfluous, saving on effort and costs. Because statistical errors linked to producing aliquots are avoided, the precision increases.

A fast and accurate heating and cooling system does not lose time in changing the temperature of the heating/cooling elements and no errors occur as the target temperature is approached (levelling out). If the heating and cooling time limited for tempering of the sample liquid is limited, the analysis period is optimized. Overshooting or undershooting the target temperatures is avoided by using constant temperature zones. Errors due to unintentional side reactions are thus greatly reduced and the number of false positive or false negative results drops.

The device of the invention is of particular application to a method for the amplification of at least one nucleic acid in a sample, comprising the following steps:

a) preparing a solid support comprising at least two primers immobilized thereon, each consisting of at least two partial sequences, wherein a first partial sequence has a nucleotide sequence at its 3' end which is complementary to the nucleic acid to be amplified and has at the 5'-end at least a second constant partial sequence which has less than 90% identity with a part section of the nucleic acid to be amplified, wherein the primer is immobilized on the solid support via the 5' end of the second partial sequence and wherein the nucleotide sequences which are complementary to the nucleic acids which are to be amplified of at least two primers immobilized on the support as forward and reverse primers are suitable for amplifying the nucleic acid to be amplified;

b) contacting the solid support with a solution comprising a sample and at least one primer, wherein the at least one primer is essentially identical to the constant partial sequence of the immobilized primer and/or to the at least two primers immobilized on the solid supports;

c) carrying out an amplification reaction to produce at least one soluble amplification product; and d) if appropriate, detecting an amplification product bound to the solid support via said at least one immobilized primer.

Methods of this type have, for example, been described in Pernov et al (Nucleic Acid Res (2005), 33:e11).

In a first amplification cycle, at least one of the first partial sequences (specific sequence) of the immobilized primer may possibly produce an amplification product on the basis of the sample nucleotide sequence. The first amplification product (extension of the immobilized primer) acts as a template for amplification (extension) of a second immobilized primer which is in the vicinity (<1 µm). In this way, an amplification product may possibly be formed between two immobilized primers. If the first amplification cycle results in an amplification product, then a second amplification cycle can start using the constant primers in the solution. In this respect, the sequence contained in the immobilized amplification product which is complementary to the sequence of the 5' end of the immobilized primer acts as a template for the constant soluble primer. The amplification product that may possibly be produced thereby is now soluble. In a third amplification cycle, the soluble amplification products produced in cycles one and two are amplified by the constant primer in a soluble PCR reaction. Since all amplification products from the solid phase reaction are amplified in solution by the same primers, the amplification rate for all target sequences is almost identical. Annealing follows under conditions that enable the primers to bind specifically to their target sequences. The primers are designed for this purpose. The skilled person will be well aware of methods which are appropriate for this purpose.

With the method of the type described above, signal generation occurs over three different amplification cycles (solid phase primer extension, solid phase PCR and constant liquid phase PCR). With the method of the invention, it is additionally possible to carry out specific, sensitive multiplex PCR since on the one hand the number of primers in solution can be significantly reduced, since the immobilized primers with the constant nucleotide sequence together with a sequence-specific primer section are suitable for amplification of all nucleic acids, and on the other hand, the amplification in solution reaches the required sensitivity (exponential amplification). The method of the invention is also equally suitable for testing for DNA and RNA in a sample.

The signal generation (i.e. test) can then occur via sequence-specific binding of the amplification products to the primers immobilized on the solid support, for example, by using specific DNA intercalators (SYBR Green I, Eva Green, etc) by dyes already incorporated into the amplification product or other specific reactions (colour reactions, chemical or physical tests) which indicate the presence of amplification products.

The advantages of the method lie on the one hand in a specific initial test with high sensitivity due to an exponential propagation in the liquid, and on the other hand in the highly parallel use of a large number of primers (>10 spots) on the solid support per cm2.

A further advantage of the method of the invention is that because of the different amplification products, their immobilized primers or amplification products have different melting temperatures. To this end, in a further cycle, each spot (immobilized primer pair) has a so-called melting curve produced for it. To this end, measurements of the spots are taken at increasing temperatures and the signal strengths are recorded in sequence. Sequence-dependent melting of the nucleotide double strands changes the signal strength, on the one hand by dissociation of the labeled amplification product or on the other hand by release of the double strand intercalator (dye, for example SYBR Green). The melting curve obtained can be compared with reference values if necessary. Thus, conclusions regarding the sequence of the amplification product and thus regarding the correctness of the amplification reaction can be drawn.

The present invention will now be illustrated with reference to the following non-limiting figures and examples.

FIG. 1 shows a device in accordance with the invention, with a container arranged therein;

FIG. 2 shows a temperature profile at a defined point of the lateral surface of the rotor in a container over 1½ turns;

Figure 3:
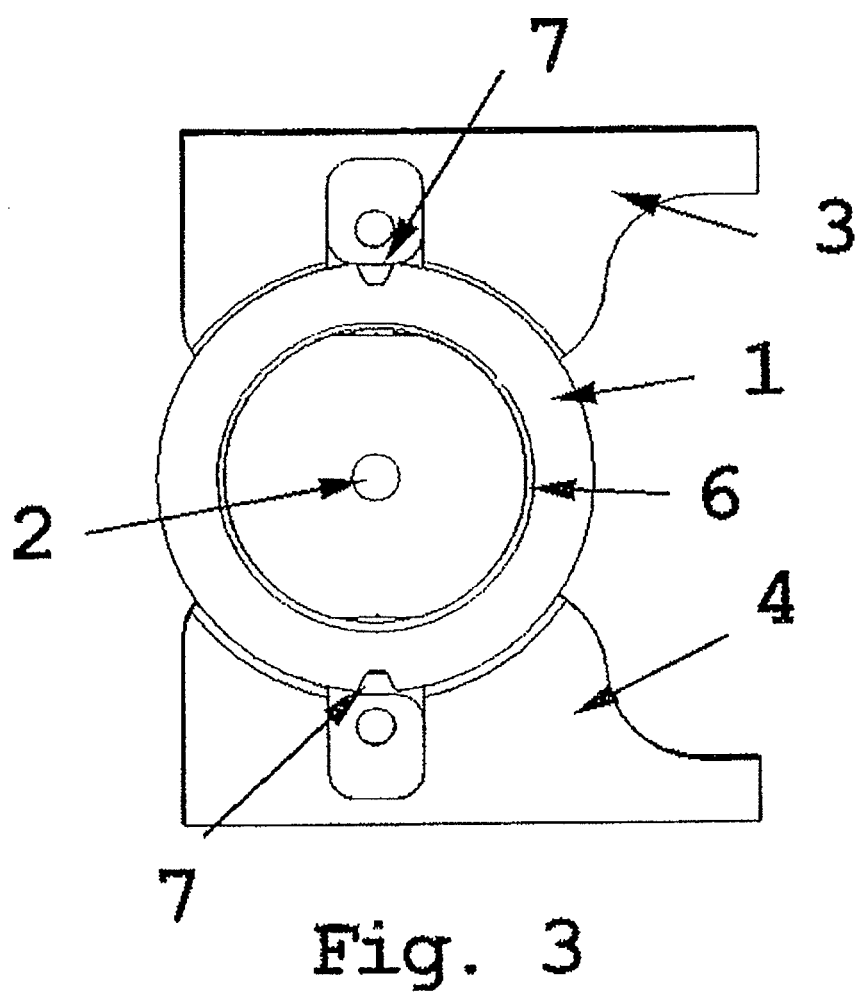
FIG. 3 shows a top view of a device in accordance with the invention with a container which contains a rotor.

FIG. 1 shows a top view of a rotor 2 in a container 1; between the inner side of the container 1 and the rotor 2 is an annular gap 6 which can be filled with liquid. The heat exchange jaws 3, 4 leave an equal sized gap 5 at the contact surfaces. The gap 5 acts on the one hand as insulation (air) and as a transitional zone from one to the other temperature; on the other hand, the gap 5 is a zone via which samples or transformation reactions can be tested from outside the container 1 or the device of the invention. The temperatures in the container 1 (in particular in the annular gap 6 between the container 1 and the rotor 2) are, for PCR, between 98° C. and 4° C., for example. The heating jaws 3, 4 lie flush against the outside of the container and may be a little taller or shorter than it. The material may be formed from an aluminium alloy, steel, copper or another material with good heat conductivity (heating and cooling films, liquid-filled, rigid or flexible containers or bags). On the rear side of the jaws 3, 4 is a heating element, such as a Peltier element. Alternatively, for example, this can be replaced by electrical resistance heating, heat radiation, ultrasound, microwave etc.

FIG. 2 shows the theoretical profile for the liquid temperature and the experimental profile. It is clear from the profile curves that both set temperatures are reached. The path of the curves between the temperatures encroaches a little on the hot zones; this is caused by diffusion of heat in the liquid and also within the container material. In addition, during movement, the liquids mix slightly, meaning that a sharp temperature boundary is not obtained. It is clear that the conditions for solid phase amplification (or OnSpot PCR) are satisfied since the liquid over the stationary phase and thus also the immobilized molecules (primers) which extend into the liquid reach the required temperatures.

FIG. 3 shows a top view of the device of the invention. The heat exchange jaws 3 and 4 surround a rotationally symmetrical container 1 containing a rotor 2, leaving a gap. A locking device 7 which can be arranged on one or both of the heat exchange jaws 3 and 4 fixes the container 1 positioned in the device in translation and/or rotation. This prevents the moving rotor 2 from also moving the container 1.

Figure 4:
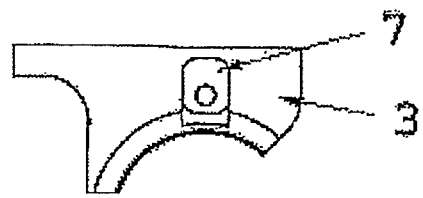

FIG. 4 shows a top view of a heat exchange jaw 3 on which a locking device 7 is provided.

Figure 5:
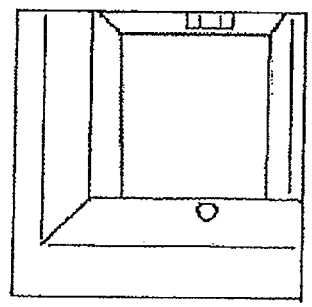
Figure 5:
Figure 5:
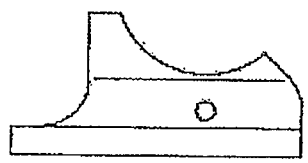
Figure 5:
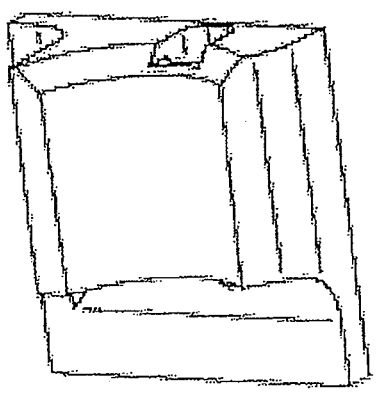

FIG. 5 shows a three-dimensional view of the heat exchange jaw 3 of the invention.

Figure 6:
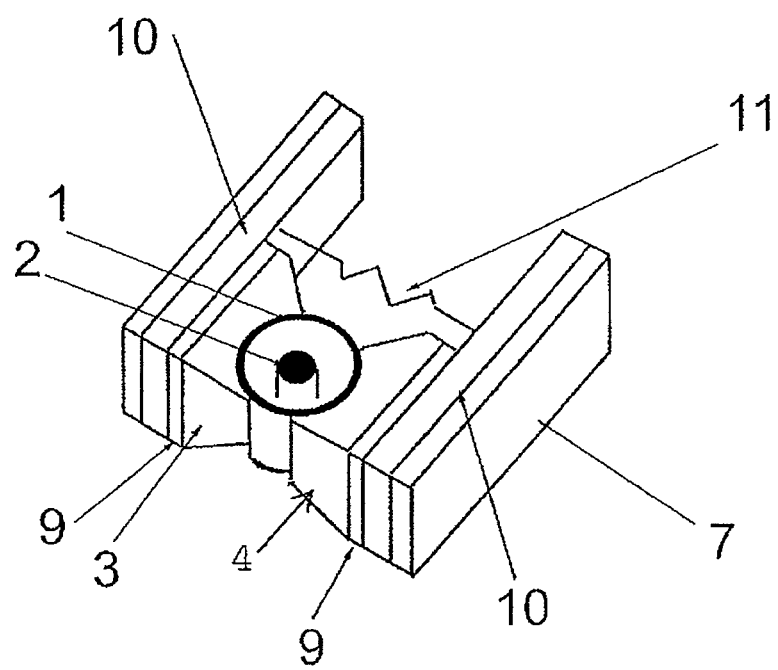

FIG. 6 shows a three-dimensional view of a device 7 in accordance with the invention. The device 7 comprises a tempering block which has two heat exchange jaws 3, 4. On each side of the heat exchange jaw 3 facing away from the container 1 which is in position is a thermal regulating element 9 (for example Peltier element). The heat exchange jaws 3, 4 are each fastened to a support element 10; these elements are connected together via a tension device 11 (for example filaments). Thus, it is possible for the jaws 3, 4 to be pressed sufficiently onto the container 1 to enable them both to reach the required temperature conditions.

Figure 7:
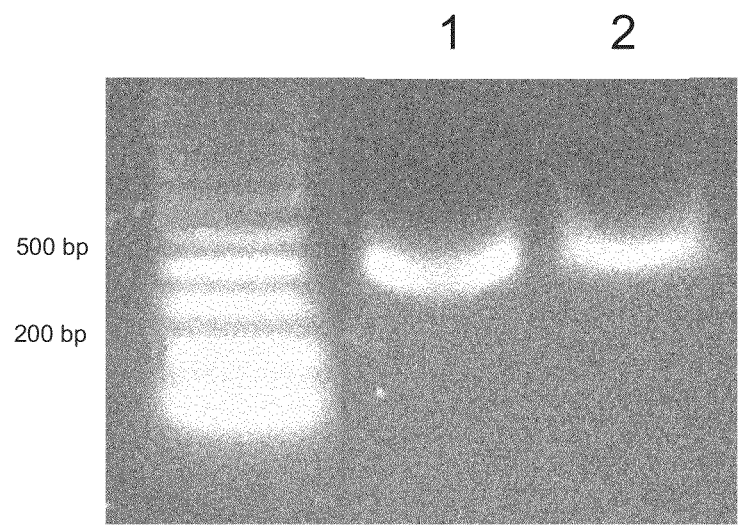

FIG. 7 shows the results of a liquid phase PCR (track 1) and a PCR carried out in the Hybcell with heating jaws controlled in different manners (track 2).

Figure 8:
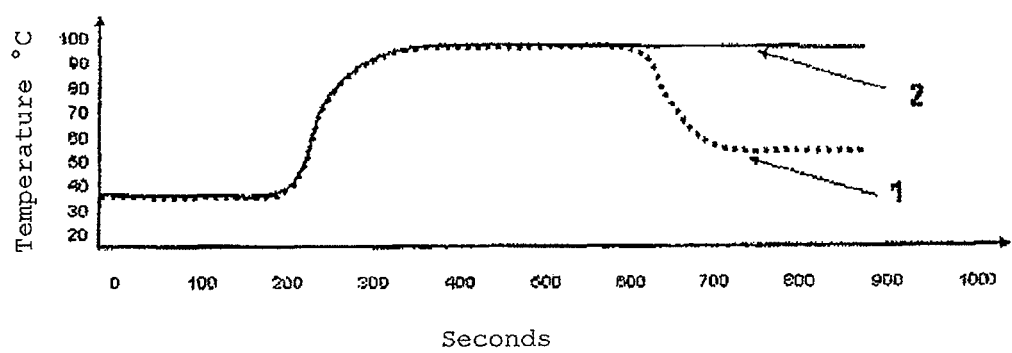

FIG. 8 shows the temperatures of the jaws during the first 1000 seconds.

EXAMPLES

Example 1

Comparison of Known Solid Phase Amplification (SPA) and Coupled SPA/PCR (OnSpot PCR)

The detection of human pathogenic agents (primarily bacteria) in blood samples is an important field of application for molecular DNA diagnostics. PCR, real time PCR and SPA are used. SPA is primarily carried out as an isolated reaction in small vessels or wells of multi-titer plates. In order to detect a large number of different pathogens, the use of SPA as a multiplex reaction in array format is recommended. The sample does not have to be divided into many individual reactions and the costs for the reagents are disproportionate to the number of tests.

Primer pairs were designed for 2 different bacteria.

The same primers were synthesized a second time, with the difference being that they additionally contained a sequence at the 5'-end that was common to all.

The solid phase (support) used was the same in all tests, namely a cylindrical body (Hybcell) coated with layer of silicon oxide. Binding of the oligomers was carried out by means of an aldehyde-amino group reaction. The spots on the surface were produced by the supplier Scienion using a piezo printer.

Next, for both systems the same reaction mixture was made up, containing: the components for a PCR reaction, fluorescence tagged nucleotides, and a defined quantity of DNA (target) to be amplified. Additionally, a defined quantity of the common primer pair was added to the OnSpot reaction. The amplification reaction was carried out by means of cycles of heating and cooling. The number of cycles required to generate a signal to noise ratio of >6 was determined.

TABLE

SPA versus OnSpot PCR

| | Cycle number | | | | | | |
|---|---|---|---|---|---|---|---|
| | 1 | 10 | 20 | 30 | 40 | 50 | 60 |
| A SPA | 0.25 | 0.26 | 0.25 | 0.29 | 0.28 | 0.41 | 0.51 |
| B SPA | 0.23 | 0.21 | 0.24 | 0.23 | 0.24 | 0.35 | 0.46 |
| A OnSpot | 0.24 | 0.25 | 0.29 | 1.45 | 7.25 | 25.00 | 56.23 |
| B OnSpot | 0.16 | 0.15 | 0.27 | 1.35 | 6.75 | 21.38 | 48.98 |

Key:
Cycle number: measurement giving the number of amplification cycles carried out;
A SPA, B SPA: test series for solid phase amplification for bacterium A (*Staph. aureus*) and B (*Enterococcus aerogenes*);
A OnSpot, B OnSpot: Test series for coupled OnSpot PCR for bacterium A (*Staph. aureus*) and B (*Enterococcus aerogenes*);

The figures in the results correspond to the ratios for the spot signal to background signal which were obtained.

Example 2

Liquid Phase PCR with Primers Comprising a Constant Partial Sequence and a Target-Specific Partial Sequence To carry out the liquid phase PCR, the same primers as those immobilized on a solid support used in Example 1 (OnSpot PCR) were employed. The difference was that all of the primers in this variation were in solution. The aim here was to use many primer pairs in parallel in a test solution with no mutual influence (non-specific amplification). This was ensured by means of a very low concentration of primers with the target-specific partial sequence and a high concentration of primers with the constant partial sequence (like the dissolved primers in the On-Spot PCR, see Example 1). The various amplification products obtained were to be identified in a second step, for example hybridization to immobilized probes (array) or gel size separation.

During the PCR, the jaws in the Hybcell were regulated to different temperatures (120° C. and 60° C.). This also resulted in a PCR (see FIGS. 7 and 8).

FIG. 7 shows an agarose gel with separated DNA fragments. The fragments were stained with SYBR Green. A standard can be seen on the left hand side. It shows the approximate sizes of the fragments. Track 1 shows a DNA fragment (amplicon) from a liquid phase PCR after 30 temperature cycles. Track 2 shows an amplicon which was produced in the Hybcell using differently regulated heating jaws and rotation of the cylinder. A preceding heating step was carried out to activate the polymerase (standard step) and then the temperatures of the jaws were regulated in different manners. The rotational rate of the cylinder was set at 1 rpm. This means that the residence time for the spots or the revolving liquid in the two temperature zones was approximately 20 seconds.

FIG. 8 shows the recorded temperature of the jaws during the first 1000 seconds; 1 is the temperature of the first jaw and 2 is the temperature of the other jaw.

The invention claimed is:

1. A device comprising:
   a rotationally symmetrical container having an exterior lateral surface and at least one tempering block for accommodating the container, said container forming a single reaction chamber; and
   at least two tempering elements, wherein the tempering elements of the at least one tempering block are in heat exchanging contact with the exterior lateral surface of the container during use, and the two tempering elements are adapted to produce at least two different, stable constant temperature zones in the single reaction chamber at the same time; and
   a rotationally symmetrical rotor inserted into the rotationally symmetrical container, wherein an annular gap is provided between the container and the rotor, and the rotor has at least one flow channel configured to convey liquids and/or gases into and/or out of the interior of the container during use, wherein the rotor is exposed to the two different, stable temperature zones when rotated due to the rotation of the rotor.

2. The device of claim 1, wherein the container can be moved in translation relative to the at least one tempering block during use.

3. The device of claim 1, wherein the rotationally symmetrical container is in the form of a cylinder.

4. The device of one of claim 1, further comprising organic molecules immobilized on a surface of the device.

5. The device of one of claim 4, wherein organic molecules are immobilized on a surface of the rotor.

6. The device of claim 4, wherein organic molecules are immobilized on a base surface of the container opposite to the tempering elements.

7. The device of claim 4, wherein organic molecules are immobilized on an inner lateral surface of the container.

8. The device of claim 4, wherein the organic molecules are nucleic acids or enzymes.

9. The device of claim 1, wherein the tempering elements are independent cooling elements or heating elements.

10. The device of claim 1, wherein the tempering elements are Peltier elements, electrical resistances, infrared emitters, microwave transmitters, elements filled with liquid or gases, light emitters or combinations thereof.

11. The device of claim 1, wherein the container is fixed relative to the at least one tempering block in heat exchanging contact with the tempering elements.

12. The device of claim 1, wherein a space is provided between the tempering elements of the at least one tempering block.

13. A method of heating and/or cooling liquid or gaseous biological samples using the device of claim 1 comprising:
  obtaining a device of claim 1;
  creating different stable temperature zones in the reaction chamber using the at least two tempering elements;
  introducing a biological sample into the reaction chamber; and
  tempering the biological sample by rotating the rotor to expose the rotor to the different stable temperature zones.

14. A method of testing for nucleic acids using the device of claim 1 comprising:
  obtaining a device of claim 1;
  creating different stable temperature zones in the reaction chamber using the at least two tempering elements;
  introducing a biological sample into the reaction chamber; and
  testier for nucleic acids.

15. A method of testing a biological sample, comprising:
  providing a rotationally symmetrical container forming a single reaction chamber;
  inserting a rotationally symmetrical rotor into the single reaction chamber;
  introducing a biological sample into the reaction chamber;
  producing a first stable temperature zone in the single reaction chamber using a first tempering element in heat exchanging contact with the container;
  producing a second stable temperature zone in the single reaction chamber using a second tempering element in heat exchanging contact with the container, wherein the first and second tempering elements are operated independently of one another at different temperatures and the first and second stable temperature zones coexist; and
  rotating the rotor so that a surface of the rotor traverses the first and second constant temperature zones.

16. The method of claim 15, wherein the container can be moved in translation relative to the at least one tempering block during use.

17. The method of claim 15, wherein the rotationally symmetrical container is a cylinder.

18. The method of claim 15, further comprising immobilizing organic molecules on a surface of the container.

19. The method of claim 18, wherein the organic molecules are nucleic acids or enzymes.

20. The method of claim 15, further comprising immobilizing organic molecules on the surface of the rotor.

21. The method of claim 15, further comprising immobilizing organic molecules on a base surface of the container.

22. The method of claim 15, further comprising immobilizing organic molecules on an inner lateral surface of the container.

23. The method of claim 15, wherein the first and second tempering elements are independent cooling elements or heating elements.

24. The method of claim 15, wherein the first and second tempering elements are Peltier elements, electrical resistance elements, infrared emitters, microwave transmitters, elements filled with liquid or gases, light emitters or combinations thereof.

25. The method of claim 15, wherein the container is fixed relative to the first and second tempering elements.

* * * * *